(12) United States Patent
Berlemann et al.

(10) Patent No.: US 9,549,962 B2
(45) Date of Patent: *Jan. 24, 2017

(54) RADIOPAQUE INJECTABLE NUCLEUS HYDROGEL COMPOSITIONS

(71) Applicant: Spine Wave, Inc., Shelton, CT (US)

(72) Inventors: Ulrich Berlemann, Bern (CH);
Thomas Wilson, Guilford, CT (US);
Peter Wronski, North Haven, CT (US);
Thomas Douville, West Haven, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/852,082

(22) Filed: Sep. 11, 2015

(65) Prior Publication Data

US 2016/0058822 A1 Mar. 3, 2016

Related U.S. Application Data

(63) Continuation of application No. 12/606,422, filed on Oct. 27, 2009, now Pat. No. 9,132,207.

(51) Int. Cl.
| | |
|---|---|
| *A61L 27/22* | (2006.01) |
| *A61K 49/04* | (2006.01) |
| *A61K 38/00* | (2006.01) |
| *A61L 27/50* | (2006.01) |
| *A61L 27/52* | (2006.01) |
| *A61F 2/44* | (2006.01) |

(52) U.S. Cl.
CPC ............... *A61K 38/00* (2013.01); *A61L 27/22* (2013.01); *A61L 27/50* (2013.01); *A61L 27/52* (2013.01); *A61F 2002/444* (2013.01); *A61K 49/04* (2013.01); *A61K 49/0433* (2013.01); *A61L 2400/06* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 6,423,333 B1 * | 7/2002 | Stedronsky | A61L 24/106 106/124.1 |
| 9,132,207 B2 * | 9/2015 | Berlemann | A61L 27/22 |
| 2004/0254523 A1 * | 12/2004 | Fitzgerald | A61B 5/0086 604/21 |
| 2005/0288789 A1 * | 12/2005 | Chaouk | A61L 27/16 623/17.16 |
| 2006/0222596 A1 * | 10/2006 | Askari | A61K 49/0457 424/9.41 |

OTHER PUBLICATIONS

LM Boyd, AJ Carter. "Injectable biomaterials and vertebral endplate treatment for repair and regeneration of the intervertebral disc." European Spine Journal, vol. 15 (Suppl 3), 2006, pp. S414-S421.*

* cited by examiner

*Primary Examiner* — Isaac Shomer
(74) *Attorney, Agent, or Firm* — Hoffmann & Baron, LLP

(57) ABSTRACT

A composition suitable for use as replacement material for all or part of a disc nucleus during percutaneous injection, the composition comprising:

an injectable, curable, cross-linkable, non-immunogenic non-toxic protein hydrogel that (i) the protein component of the protein hydrogel contains at least one crosslinkable amino acid (ii) has a static compressive modulus of at least about 10 kPa, and (iii) has a dynamic compressive modulus of at least about 10 kPa;

an iodinated contrast solution comprising an amount of an iodine compound sufficient to increase radiopacity to a discernable level, wherein the solution causes a decrease in the static and/or dynamic compressive modulus; and an amount of a crosslinker sufficient to restore at least about 100% of the decrease in static and/or dynamic compressive modulus caused by addition of the iodinated contrast solution.

26 Claims, No Drawings

SEQUENCE LISTING

```
<160> NUMBER OF SEQ ID NOS: 7

<210> SEQ ID NO 1
<211> LENGTH: 6
<212> TYPE: PRT
<213> ORGANISM: Artificial Sequence
<220> FEATURE:
<223> OTHER INFORMATION: Naturally occurring silk

<400> SEQUENCE: 1

Gly Ala Gly Ala Gly Ser
1               5

<210> SEQ ID NO 2
<211> LENGTH: 5
<212> TYPE: PRT
```

```
<213> ORGANISM: Artificial Sequence
<220> FEATURE:
<223> OTHER INFORMATION: Naturally occuring elastin

<400> SEQUENCE: 2

Gly Val Gly Val Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Naturally occurring keratin

<400> SEQUENCE: 3

Lys Leu Glu Leu Ala Glu Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: x denotes lysine, histidine, aspartic acid,
      glutamic acid, arginine, serine, threonine, and cysteine.

<400> SEQUENCE: 4

Gly Xaa Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X denotes lysine, histidine, aspartic acid,
      glutamic acid, arginine, serine, threonine, and cysteine.

<400> SEQUENCE: 5

Gly Val Gly Xaa Pro
1               5

<210> SEQ ID NO 6
<211> LENGTH: 5
<212> TYPE: PRT
<213> ORGANISM: Artificial Sequence
<220> FEATURE:
<223> OTHER INFORMATION: P27K

<400> SEQUENCE: 6

Gly Lys Gly Val Pro
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic
```

-continued

```
<400> SEQUENCE: 7

Gly Val Gly Lys Pro
1               5
```

RADIOPAQUE INJECTABLE NUCLEUS HYDROGEL COMPOSITIONS

CROSS-REFERENCE TO RELATED APPLICATIONS

This application is a continuation of U.S. Ser. No. 12/606,422, filed Oct. 27, 2009, now U.S. Pat. No. 9,132,207, issued Sep. 15, 2015, the entire contents of which is incorporated by reference herein.

FIELD OF THE INVENTION

The present invention relates generally to a protein hydrogel composition that is utilized in the treatment of spinal diseases and injuries, and specifically to the restoration of the spinal disc. More specifically, the invention contemplates compositions and methods for restoring the normal intervertebral disc space height and for facilitating the introduction of biomaterials for use in the repair and restoration of the intervertebral disc preferably via a percutaneous injection of the hydrogel without an invasive surgical procedure.

BACKGROUND OF THE INVENTION

There are many causes of disruption or degeneration of the intervertebral disc that can be generally categorized as mechanical, genetic and biochemical. One such cause is the loss of the material made in the disc, which is called the disc nucleus pulposus.

Many injectable biomaterials have been developed as a substitute for the disc nucleus pulposus. Such materials include various proteins, including hyaluronic acid, fibrin glue, alginate, elastin-like polypeptides, collagen type I gel and others. See, for example, U.S. Pat. Nos. 5,773,249; 6,380,154 B1; and 6,184,348.

The invasiveness of introducing such materials into a disc may be minimized by injecting the material percutaneously, such as for treatment of degenerative disc disease (DDD). There thus remains a need for material that is strong and durable, and that can be visualized during the percutaneous procedure.

SUMMARY OF THE INVENTION

In accordance with the invention, a composition suitable for use as replacement material for all or part of a disc nucleus is provided.

The composition includes an injectable, curable, cross-linkable, non-immunogenic non-toxic protein hydrogel.

The composition includes a protein component comprising a minimum of about 10% and a maximum of about 25% of the hydrogel by weight.

The compositions includes an iodinated contrast solution having a discernable radiopacity level and comprising a minimum of about 5% and a maximum of about 35% of the hydrogel by weight.

The composition includes a crosslinker comprising a minimum of about 0.1% and a maximum of about 10% of the hydrogel by weight.

The composition includes an injectable, curable, cross-linkable, non-immunogenic non-toxic protein hydrogel that has a static compressive modulus of at least about 10 kPa, and a dynamic compressive modulus of at least about 10 kPa, The protein hydrogel of the composition contains at least one of the following residues: lysine, histidine, serine, aspartaic acid, glutamic acid, arginine, threonine, cysteine;

The composition also includes an iodinated contrast solution comprising an amount of an iodine compound sufficient to increase radiopacity to a discernable level, wherein the solution causes a decrease in the static and/or dynamic compressive modulus; and The composition also includes an amount of a crosslinker sufficient to restore at least about 100% of the decrease in static and/or dynamic compressive modulus caused by addition of the iodinated contrast solution.

DETAILED DESCRIPTION OF THE PREFERRED EMBODIMENTS

The inventive compositions are useful in replacing a portion or substantially all of the natural material in an intervertebral disc nucleus, i.e., the nucleus pulposus. The intervertebral discs lie between adjacent vertebrae in the spine. Such discs include, for example, lumbar discs, thoracic discs, cervical discs, and sacral discs.

The compositions of the invention are suitable for use as replacement material for all or part of a disc nucleus (i.e., of the nucleus pulposus) preferably during percutaneous injection. During such procedures, the compositions are injected into a damaged disc.

Methods and instruments for injecting curable biomaterial into a damaged disc in a percutaneous procedure are more particularly described in published patent application US2006/009851, filed on Jun. 29, 2005, commonly assigned to the same assignee as the present invention and incorporated herein by reference in its entirety for all purposes.

The Protein Hydrogel

The compositions comprise a protein hydrogel, i.e., a colloidal gel in which water is the dispersion medium, or a mixture of protein hydrogels. The protein hydrogels preferably possess a degree of flexibility similar to that of natural tissue, due to their significant water content.

In one embodiment a protein component includes a minimum of about 10% and a maximum of about 25% of the hydrogel by weight.

In one embodiment, the protein hydrogel is constructed using a protein block copolymer that comprises at least 2, and preferably 4, of the following segments:
  (i) a segment having at least 1 sequence comprising the six amino acid repetitive sequence found in naturally occurring silk;
  (ii) a segment having at least 1 sequence comprising the five amino acid repetitive sequence found in naturally occurring elastin;
  (iii) a segment having at least 1 sequence comprising the 3 amino acid repetitive sequence found in naturally occurring collagen; or
  (iv) a segment having at least 1 sequence comprising the 7 amino acid repetitive sequence found in naturally occurring keratin; or
  combinations of any two, three, or all four of the above.

In another embodiment, the protein hydrogel is constructed using a protein block copolymer, preferably a block copolymer that comprises the following segments:
  (i) a segment having at least 2 sequences, wherein each of the sequences is comprised of the six amino acid repetitive sequence found in naturally occurring silk;

(ii) a segment having at least 2 sequences, wherein each of the sequences is comprised of the five amino acid repetitive sequence found in naturally occurring elastin;
(iii) a segment having at least 2 sequences, wherein each of the sequences is comprised of the 3 amino acid repetitive sequence found in naturally occurring collagen; or
(iv) a segment having at least 2 sequences, wherein each of the sequences is comprised of the 7 amino acid repetitive sequence found in naturally occurring keratin; or combinations of any two, three, or all four of the above.

Preferably, the protein component of the protein hydrogel comprises a total of at least 50 sequences, and a maximum number of 500 sequences.

In addition, the protein component of the protein hydrogel comprises at least one amino acid residue that contains a functional group that can be cross linked. Some examples of naturally occurring functional groups include amino groups on lysine and histidine residues, carboxyl groups on aspartate and glutamate residues, guanidino groups on arginine residues, hydroxyl groups on serine and threonine residues, and thiol groups on cysteine residues.

If the protein does not contain a functional group that is available for cross linking, an amino acid residue of the protein, including possibly an amino acid of a sequence described above, is replaced with an amino acid that contains such a functional group. The protein has at least one amino acid that contains a cross-linkable functional group. Preferably, the protein has at least 0.1%, more preferably at least 1%, and most preferably at least about 2% amino acids that contain a cross-linkable functional group. Usually, the protein has no more than 20%, preferably no more than 10%, and more preferably no more than 5% amino acids that contain a cross-linkable functional group.

An example of a sequence of amino acids found in naturally occurring silk (Sk) is GlyAlaGlyAlaGlySer (SEQ ID NO: 1). An example of a sequence of amino acids found in naturally occurring elastin (Es) is GlyValGlyValPro (SEQ ID NO: 2). An example of a sequence of amino acids found in naturally occurring collagen (Cl) is GlyAlaPro. An example of a sequence of amino acids found in naturally occurring keratin (Kr) is LysLeuGluLeuAlaGluAla (SEQ ID NO: 3).

In one aspect, the protein component of the protein hydrogel has the formula:

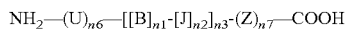
NH$_2$—(U)$_{n6}$—[[B]$_{n1}$-[J]$_{n2}$]$_{n3}$-(Z)$_{n7}$—COOH wherein:
U and Z represent amino acid sequences other than Sk, Es, Cl, or Kr, and preferably sequences that are useful in cloning the protein;
B independently at each position represents Sk, Es, Cl, or Kr;
J independently at each position represents Sk, Es, Cl, or Kr, but not the sequence in B;
Sk represents GlyAlaGlyAlaGlySer (SEQ ID NO: 1);
Es represents GlyValGlyValPro (SEQ ID NO: 2);
Cl represents GlyAlaPro;
Kr represents LysLeuGluLeuAlaGluAla SEQ ID NO: 3); and
n1 represents 1-12, and more usually 2-6, and more usually 2-4;
n2 represents 1-16, and more usually 2-12, and more usually 4-8;

n3 represents 1-30, more usually 4-20, and more usually 12-18;
n6 and n7 independently represent 0 or 1; and
wherein at least one of the sequences represented by B or J comprises, or is modified to comprise, at least one crosslinkable amino acid residue, e.g., lysine, histidine, aspartatic acid, glutamic acid, arginine, serine, threonine, or cysteine.

In one embodiment, B represents Sk or Es. In another embodiment, J represents Sk or Es. In a preferred embodiment, B and J represent Sk or Es. In a more preferred embodiment, B represents Sk and J represents Es.

In another aspect, the protein component of the protein hydrogel has the formula:

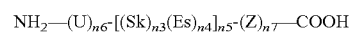
NH$_2$—(U)$_{n6}$-[(Sk)$_{n3}$(Es)$_{n4}$]$_{n5}$-(Z)$_{n7}$—COOH wherein:
n3 represents 1-12;
n4 represents 1-16;
n5 represents 1-30;
n6 and n7 represent 0 or 1; and
wherein at least one of the sequences represented by Sk or Es is modified to comprise at least one crosslinkable amino acid residue, e.g., lysine, histidine, aspartatic acid, glutamic acid, arginine, serine, threonine, or cysteine.

In a more particular aspect, the protein component of the protein hydrogel has the formula:

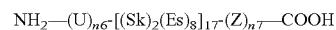
NH$_2$—(U)$_{n6}$-[(Sk)$_2$(Es)$_8$]$_{17}$-(Z)$_{n7}$—COOH wherein at least one of the sequences represented by Sk or Es is modified to comprise at least one crosslinkable amino acid residue, e.g., lysine, histidine, aspartatic acid, glutamic acid, arginine, serine, threonine, or cysteine. In a preferred embodiment of this aspect, at least one Es segment is replaced by an amino acid sequence selected from the group consisting of GlyXGlyValPro (SEQ ID NO: 4) or GlyValGlyXPro (SEQ ID NO: 5) wherein X represents lysine, histidine, aspartic acid, glutamic acid, arginine, serine, threonine, and cysteine; and preferably GlyLysGlyValPro (SEQ ID NO: 6) or GlyValGlyLysPro (SEQ ID NO: 7).

In an even more particular aspect, the protein component of the protein hydrogel has the formula:

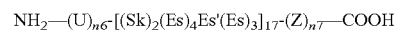
NH$_2$—(U)$_{n6}$-[(Sk)$_2$(Es)$_4$Es'(Es)$_3$]$_{17}$-(Z)$_{n7}$—COOH wherein Es' represents GlyLysGlyValPro (SEQ ID NO: 6) or GlyValGlyLysPro (SEQ ID NO: 7). Preferably, Es' represents GlyLysGlyValPro (SEQ ID NO: 6) (Such protein is known as P27K). The invention also covers protein hydrogels having an amino acid sequence that is at least 90% identical to the amino acid sequence of P27K, and preferably at least 95% identical to the amino acid sequence of P27K.

The protein component of the protein hydrogels in accordance with the present invention will have minimum molecular weights of at least about 20 kD, generally at least about 30 kD, preferably at least about 50 kD. The maximum molecular weights are usually not more than about 205 kD, more usually not more than about 150 kD, preferably not more than about 100 kD, and even more preferably not more than about 77 kD. The protein component of the protein hydrogels will have at least two functional groups available for crosslinking, more usually at least about four function groups available for crosslinking. The equivalent weight per functional group is generally in the range of about 1 kD to 40 kD, more usually in the range of about 5 kD to 25 kD, preferably in the range of about 7 kD to 10 kD.

In accordance with one embodiment of the present invention, it is important to maintain the mechanical strength of the protein hydrogel during the percutaneous replacement of the nuclear material and to maintain adhesion of the implant to a collagen substrate. Adhesion of the implant to a collagen substrate is an important component in keeping the implant in place within the disc. Adhesion of the implant is a component of extrusion resistance testing. Subsequent to adding the iodinated contrast solution and the crosslinker, the protein hydrogel preferably has a minimum static and a minimum dynamic compressive modulus each of about 10 kPa, and preferably each about 20 kPa. The maximum static and a dynamic compressive modulus is each about 500 kPa, and preferably each about 300 kPa. Static and Dynamic Compressive Moduli are the ratio of stress to strain in compression under static and vibratory conditions, respectively. (See, for example, Meyers and Chawla (1999): "Mechanical Behavior of Materials," pp 98-103).

Iodinated Contrast Agents

The injectable compositions of the present invention further contain an organic contrast agent, preferably an iodinated contrast agent, suitable for use in imaging methods known in the art in order to provide acceptable visibility in the lumbar spine during injection. The iodinated contrast agent is useful in distinguishing surrounding tissue that is subjected to detectable forms of radiation such as, for example, X radiation, radioactivity, infrared radiation, ultraviolet radiation, electron or neutron radiation, or a magnetic field. The iodinated contrast agents are useful in imagine methods such as fluoroscopy, X-ray radiography, computerized tomography (CT), ultrasound, etc.

In one embodiment, an iodinated contrast agent is non-ionic. As used herein, non-ionic refers to an organic compound that contains one to three covalently bonded iodine atoms. Exemplary iodine based contrast agents include but are not limited to diatrizoate, iodecol, iodixanol, iofratol, iogulamide, iohexol, iomeprol, iopamidol, iotrol, ioversol, ioxaglate, and metrizamide. A preferred iodinated contrast agent is Isovue 370. For example, the volume of Isovue 370 required to yield a final iodine concentration of 60 mg I/mL of protein polymer causes an approximate 30% decrease in modulus and adhesion strength, and a minimal effect on extrusion resistance.

In another embodiment, the iodine agent is ionic. As used herein, ionic refers to a salt that contains one to three iodide ions. Some examples of iodide salts include sodium iodide, potassium iodide, and ammonium iodide.

In one embodiment, there are substantially no covalent bonds between an atom of the iodine compound and an atom of the protein hydrogel.

An iodinated contrast agent is added to the protein in an amount sufficient to make the composition radiopaque. As used herein, the term "radiopacity" refers to the relative inability of electromagnetic radiation, particularly X-rays, to pass through a particular material. Dense materials that prevent the passage of electromagnetic radiation are called 'radiopaque.' The term refers to the relative opaque white appearance in radiographic imaging, when passing X-rays through dense matter. Radiopaque substances are those that will not allow X-rays or similar radiation to pass.

The compositions of the present invention are radiopaque when radiopacity is increased to a discernable level, i.e., a level that is detectable by suitable imaging methods, e.g., fluoroscopy, CT, X-ray, etc.

In one embodiment, an iodinated contrast solution having a discernable radiopacity level and includes a minimum of about 5% and a maximum of about 35% of the hydrogel by weight.

In a preferred embodiment, radiopacity is transient. As used herein, transient refers to a state of being brief and short-lived. For example, the hydrogel maintains radiopacity for a maximum of usually not more than 30 days, more usually not more than 14 days, preferably not more than 7 days and more preferably not more than 2 days.

Crosslinker

The crosslinker is a molecule that has at least two groups, each of which is able to form a covalent bond with a crosslinkable functional group on the protein, e.g., an amino, carboxyl, guanidino, hydroxyl, or thio group. The functional groups for crosslinking may be all the same or combinations of functional groups that are able to form covalent bonds with the functional groups and may include the functional groups, such as amino, e.g. lysine, histidine; carboxyl, e.g. aspartate and glutamate; guanidino, e.g. arginine; hydroxyl, e.g. serine and threonine; and thiol, e.g. cysteine. For example, the crosslinker may have a functional group that reacts with a naturally occurring functional group on an amino acid of the protein component of the protein hydrogel.

Various reactive functional groups may be employed on the crosslinker, such as aldehyde, isocyanate, mixed carboxylic acid anhydride, e.g. ethoxycarbonyl anhydride, activated olefin, halo, amino, and the like. By appropriate choice of the functional groups on the protein polymer, and the crosslinking agent, rate of reaction and degree of crosslinking can be controlled.

In one embodiment, the crosslinker has the formula: $X^1$—R—$X^2$; wherein $X^1$ and $X^2$ are functional groups that form covalent bonds with the functional groups of the protein component of the protein hydrogel. R represents a saturated or unsaturated hydrocarbyl chain (i.e. alkyl or alkenyl) having a minimum of 2, preferably 3, and more preferably 4 carbon atoms in the chain; and a maximum of 24, preferably a maximum of 12, and more preferably a maximum of 8. The carbon atoms in the hydrocarbyl chain may optionally be replaced by at least one heteroatom; wherein heteroatoms are selected from the group consisting of —O— or —NH—; and wherein each heteroatom is separated from each other heteroatom by at least two carbon atoms. In one embodiment, $X^1$ and $X^2$ are ester groups or isocyanate groups.

Various crosslinking agents may be employed, particularly those which have been used previously and have been found to be physiologically acceptable. Some useful functional groups on the crosslinker include, for example dialdehydes, such as glutaraldehyde, activated diolefins, diisocyanates such as, tetramethylene diisocyanate, hexamethylene diisocyanate, octamethylene diisocyanate, acid anhydrides, such as succinic acid dianhydride, ethylene diamine tetraacetic acid dianhydride, diamines, such as hexamethylene diamine, cyclo(L-lysyl-L-lysine) isocyanate groups (e.g., tetramethylene diisocyanate, hexamethylene diisocyanate, octamethylene diisocyanate) aldehyde groups (glutaraldehyde); acid anhydrides. Preferably, the functionality is amino. (including guanidine), etc. The crosslinking agent may also contain unsymmetrical functional groups, for example, activated olefin aldehydes, e.g. acrolein and quinoid aldehydes, activated halocarboxylic acid anhydride, and the like. The crosslinking agents will usually be commercially available or may be readily synthesized in accordance with conventional ways, either prior to application of the adhesive or by synthesis in situ.

Thus, depending upon the function groups on the protein and on the crosslinking agent, one can form amides, imines, ureas, esters, ethers, urethanes, thio ethers, disulfides, and the like.

The crosslinking agent contains two or more functional groups, usually not exceeding four functional groups. The functional groups may be the same or different. The ratio of crosslinking agent to protein component of the protein hydrogel will vary widely, depending upon the crosslinking agent, the number of functional groups present on the protein component of the protein hydrogel, the desired rate of curing, and the like. Generally, the weight ratio of the protein component of the protein hydrogel to crosslinking agent will be at least about 1 to 1, usually at least about 10 to 1, and generally at least about 20 to 1; and not greater than about 250 to 1, usually not greater than about 150 to 1, and generally not greater than about 50 to 1. Considerations in selecting the protein-crosslinking agent equivalent ratio will be the rate of setup, reactivity of the crosslinking agent, relative solubility of the crosslinking agent in the mixture, physiological properties of the crosslinking agent, desired degree of stability of the crosslinked product, and the like.

In one embodiment a crosslinker is included in an amount of a minimum of about 0.1% and a maximum of about 10% of the hydrogel by weight.

The mixing together of the iodinated contrast solution and the protein component of the protein hydrogel causes a dilution of the protein component of the protein hydrogel, and results in a corresponding loss of mechanical strength of the resultant hydrogel. Accordingly, the compositions of the invention comprise a sufficient amount of a crosslinker to restore at least about 100%, and preferably at least about 150%, of the decrease in static and/or dynamic compressive modulus caused by addition of the iodinated contrast solution.

Increasing the crosslinker can be used to offset the dilution effects, or to improve the material properties in hydrogels containing diluted protein concentrations. The strength reduction is dependent on the amount of dilution. The amount of dilution will vary with iodine concentration within the iodinated contrast chosen. In particular, the lower the iodine concentration in the contrast solution, the more fluid will need to be added to attain the necessary level of iodine in the implant material. With the increased crosslinker, adhesion to collagen may be increased about 30% and the extrusion resistance increased about 100% above the original non-diluted material.

Composition

The compositions are injectable, curable, non-immunogenic, and non-toxic. Injectable means that, during replacement of the nucleus pulposus such as in a percutaneous procedure, the compositions can be infused into a nucleus from a syringe, pump, or similar device, preferably as a liquid.

The composition is also curable. Curable means a change in state, condition, and/or structure in an advantageous way. The curing process is induced by at least one variable, such as addition of crosslinker, heat, radiation, the presence of a curing catalyst or accelerator, or the like. Curing may be partial as well as complete. The injection of curable compositions is described in published application US2006/0009851 identified hereinabove.

The compositions of the invention are non-immunogenic, i.e., the compositions do not cause a significant immune response. The compositions are also "non-toxic," i.e., the compositions do not injure the subject of the nuclear replacement, usually a person or a laboratory animal. If the iodinated contrast agent is transient, it will contribute little to immunogenicity or toxicity.

The composition in accordance with the present invention may vary widely as long as the composition achieves the claimed criteria. A suitable example of such a composition has, for example by weight, a minimum of about 30% water, and a maximum of about 85% water; a minimum of about 10% protein and a maximum of about 25% of protein; a minimum of about 5% iodinated contrast agent and a maximum of about 35% of iodinated contrast agent; and a minimum of about 0.1% crosslinker and a maximum of about 10% crosslinker. The composition may also include buffer salts and/or other formulation additives in the range of about 0.1%-10% by weight. Such buffer salts and formulation additives may include sodium and/or potassium phosphate, sodium acetate, sodium chloride, tromethamine, sodium citrate, sucrose and mannose.

While the composition of the present invention has been described herein particularly with respect to percutaneous injection, it should be appreciated that the subject composition may also be used as an injectable composition in non-percutaneous procedures, such as in open surgical procedures for the treatment of degenerative disc diseases (DDD) or as an adjunct to microdiscectomy (AMD) procedures, also described in the aforementioned published application US2006/0009851.

EXAMPLES

The following Examples are directed to radiopaque injectable nucleus hydrogel compositions of some embodiments of the present invention.

Examples 1A-1D

Radiopaque injectable nucleus hydrogel compositions are prepared in accordance with the compositions indicated in Examples 1A-1D, with Iopamidol (Isovue®) and Iohexol (Omnipaque®) as the contrast agents; hexamethylene diisocyanate as the crosslinker; and sodium phosphate as the salt buffer.

Composition of Example 1A

| Component | Weight % |
| --- | --- |
| P27K | 17 |
| Iohexol (Omnipaque ®) | 3 |
| hexamethylene diisocyanate | 0.7 |
| sodium phosphate | 1 |
| Water | Remainder |

Composition of Examples 1B

| Component | Weight % |
| --- | --- |
| P27K | 14.8 |
| Iohexol (Omnipaque ®) | 6 |
| hexamethylene diisocyanate | 0.7 |
| salts sodium phosphate | 1 |
| Water | Remainder |

Composition of Examples 1C

| Component | Weight % |
| --- | --- |
| P27K | 16 |
| Iopamidol (Isovue ®). | 5 |
| hexamethylene diisocyanate | 4.3 |
| sodium phosphate | 1 |
| Water | Remainder |

Composition of Examples 1D

| Component | Weight % |
| --- | --- |
| P27K | 16 |
| Iopamidol (Isovue ®) | 5 |
| hexamethylene diisocyanate | 2.2 |
| sodium phosphate | 1 |
| Water | Remainder |

Examples 2A-2E

Radiopaque injectable nucleus hydrogel compositions are prepared in accordance with the compositions indicated in Examples 2A-2E with Iodixanol (Visipaque®) and Iotrolan (Osmovist®) as the contrast agents; hydrogenated diphenylmethane diisocyanate, tolylene diisocyanate, and glutaraldehyde as the crosslinker; and sodium citrate, sodium acetate, and tromethamine as the buffer salt.

Composition of Example 2A

| Component | Weight % |
| --- | --- |
| P27K | 17 |
| Iodixanol (Visipaque ®) | 3 |
| hydrogenated diphenylmethane diisocyanate | 0.7 |
| sodium citrate | 1 |
| Water | Remainder |

Composition of Examples 2B

| Component | Weight % |
| --- | --- |
| P27K | 14.8 |
| Osmovist ® | 6 |
| tolylene diisocyanate | 0.7 |
| sodium acetate | 1 |
| Water | Remainder |

Composition of Examples 2C

| Component | Weight % |
| --- | --- |
| P27K | 16 |
| Iodixanol (Visipaque ®) | 5 |
| hydrogenated diphenylmethane diisocyanate | 4.3 |
| sodium citrate | 1 |
| Water | Remainder |

Composition of Examples 2D

| Component | Weight % |
| --- | --- |
| P27K | 16 |
| Iotrolan (Osmovist ®) | 5 |
| tolylene diisocyanate | 2.2 |
| sodium acetate | 1 |
| Water | Remainder |

Composition of Examples 2E

| Component | Weight % |
| --- | --- |
| P27K | 16 |
| Osmovist ® | 5 |
| glutaraldehyde | 2.2 |
| tromethamine | 1 |
| Water | Remainder |

What is claimed is:

1. A composition suitable for use as replacement material for all or part of a disc nucleus pulposus, the composition being radiopaque, injectable, non-immunogenic, non-toxic, and cross-linked, wherein the composition is made by:
(a) providing a cross-linkable protein hydrogel comprising a protein selected from the group consisting of
a segment having at least 1 sequence comprising the three amino acid repetitive sequence found in naturally occurring collagen,
a segment having at least 1 sequence comprising the seven amino acid repetitive sequence found in naturally occurring keratin, and combinations thereof;
wherein said protein hydrogel has a static compressive modulus of at least about 10 kPa, and a dynamic compressive modulus of at least about 10 kPa;
(b) providing an iodinated contrast solution comprising an amount of an iodine compound wherein the combination of the protein hydrogel and the iodinated contrast solution has a discernable radiopacity, and has a static or dynamic compressive modulus that is decreased compared to that of the protein hydrogel alone;
(c) providing a crosslinker; and
(d) crosslinking the composition with using the crosslinker provided in step (c);
wherein the radiopaque crosslinked composition has a static compressive modulus of at least about 10 kPa and a dynamic compressive modulus of at least about 10 kPa.

2. The composition of claim 1, wherein the composition is suitable for use during percutaneous injection.

3. The composition of claim 1, wherein the static compressive modulus has a maximum value of at least about 500 kPa, and the dynamic compressive modulus has a maximum value of at least about 500 kPa.

4. The composition of claim 1, wherein the protein of the protein hydrogel has a minimum molecular weight of about 20,000 Daltons and a maximum molecular weight of about 205,000 Daltons.

5. The composition of claim 1, wherein the iodine compound is ionic.

6. The composition of claim 5, wherein the iodine compound is selected from the group consisting of sodium iodide, potassium iodide, and ammonium iodide.

7. The composition of claim 1, wherein the iodine compound is selected from the group consisting of iopamidol, diatrizoate, iodecol, iodixanol, iofratol, iogulamide, iohexol, iomeprol, iotrol, ioversol, ioxaglate, and metrizamide.

8. The composition of claim 1, wherein the iodine compound is non-ionic.

9. The composition of claim 8, wherein the iodine compound is iopamidol.

10. The composition of claim 8, wherein there are substantially no covalent bonds between an atom of the iodine compound and an atom of the protein hydrogel.

11. The composition of claim 1, wherein the crosslinker is selected from the group consisting of tetramethylene diisocyanate, hexamethylene diisocyanate, octamethylene diisocyanate, tolylene diisocyanate, diphenylmethane diisocyanate, glutaraldehyde, succinic acid dianhydride, ethylene diamine tetraacetic acid dianhydride, bis(sulfosuccinimidyl) suberate, ethyleneglycol bis(sulfosuccinimidyl) succinate, disulfosuccinimidyl tartrate, EDC (1-ethyl-3-[3-dimethylaminopropyl]carbodiimide), sulfosuccinic acid and combinations thereof.

12. The composition of claim 1, wherein the crosslinker has the formula:
$X^1$—R—$X^2$; wherein $X^1$ and $X^2$ are groups that form covalent bonds with $NH_2$ or OH groups, and R represents a saturated or unsaturated hydrocarbyl chain having a minimum of 2 carbon atoms in the chain; and a maximum of 24 carbon atoms in the chain; wherein the carbon atoms in the hydrocarbyl chain may optionally be replaced by at least one heteroatom; wherein heteroatoms are selected from the group consisting of —O— and —NH—; and wherein each heteroatom is separated from each other heteroatom by at least two carbon atoms.

13. The composition of claim 12, wherein $X^1$ and $X^2$ are ester groups or isocyanate groups.

14. The composition of claim 12, wherein the crosslinker is hexamethylene diisocyanate.

15. The composition of claim 12, wherein the hydrocarbyl chain has a minimum of 3 carbon atoms in the chain.

16. The composition of claim 12, wherein the hydrocarbyl chain has a minimum of 4 carbon atoms in the chain.

17. The composition of claim 12, wherein the hydrocarbyl chain has a maximum of 12 carbon atoms in the chain.

18. The composition of claim 12, wherein the hydrocarbyl chain has a maximum of 8 carbon atoms in the chain.

19. The composition of claim 1, further comprising water in an amount between about 30% and about 85%.

20. The composition of claim 1, wherein protein is present in an amount of between about 10% and about 25%.

21. The composition of claim 1, wherein the composition further comprises an additive selected from the group consisting of sodium phosphate, potassium phosphate, sodium acetate, sodium chloride, sodium citrate, sucrose, and mannose.

22. The composition of claim 21, wherein the additive is present in an amount of 0.1% to 10% by weight of the composition.

23. The composition of claim 1, wherein the disc is selected from the group consisting of a lumbar disc, a thoracic disc, a cervical disc, and a sacral disc.

24. A method for preparing a radiopaque, injectable, non-immunogenic, non-toxic and crosslinked composition, the method comprising:
(a) providing a cross-linkable protein hydrogel comprising a protein selected from the group consisting of
(i) a segment having at least 1 sequence comprising the three amino acid repetitive sequence found in naturally occurring collagen,
(ii) a segment having at least 1 sequence comprising the seven amino acid repetitive sequence found in naturally occurring keratin,
(iii) $NH_2$—$(U)_{n6}$-$[(Sk)_2(Es)_8]_{17}$-$(Z)_{n7}$—COOH, and (iv) NH$_2$—(U)$_{n6}$-[(Sk)$_2$(Es)$_4$Es'(Es)$_3$]$_{17}$-(Z)$_{n7}$—COOH wherein: U and Z represent sequences useful in cloning the protein;
Sk represents GlyAlaGlyAlaGlySer (SEQ ID NO: 1);
Es represents GlyValGlyValPro (SEQ ID NO: 2);
Es' represents GlyLysGlyValPro (SEQ ID NO: 6) or GlyValGlyLysPro (SEQ ID NO: 7);
n6 and n7 independently represent 0 or 1; and
wherein said protein hydrogel has a static compressive modulus of at least about 10 kPa, and a dynamic compressive modulus of at least about 10 kPa;

(b) providing an iodinated contrast solution comprising an amount of an iodine compound wherein the combination of the protein hydrogel and the iodinated contrast solution has a discernable radiopacity, and has a static or dynamic compressive modulus that is decreased compared to that of the protein hydrogel alone;

(c) providing a crosslinker; and
(d) crosslinking the composition with using the crosslinker provided in step (c);

wherein the radiopaque crosslinked composition has a static compressive modulus of at least about 10 kPa and a dynamic compressive modulus of at least about 10 kPa.

25. A method for restoring normal intervertebral disc space height, the method comprising percutaneously injecting into a disc nucleus pulposus the composition prepared according to claim 24.

26. A method for repairing or restoring an intervertebral disc, the method comprising percutaneously injecting into a disc nucleus pulposus the composition prepared according to claim 24.

* * * * *